United States Patent [19]

Handley et al.

[11] Patent Number: 4,748,276

[45] Date of Patent: May 31, 1988

[54] PROCESS FOR PREPARING N,N-BIS(2-HYDROXYETHYL)BENZYLAMINE AND N,N-BIS(2-CHLOROETHYL)BENZYLAMINE

[75] Inventors: John R. Handley, Schodack; Allen F. Dow, Kinderhook, both of N.Y.

[73] Assignee: Sterling Drug Inc., New York, N.Y.

[21] Appl. No.: 708,633

[22] Filed: Mar. 6, 1985

Related U.S. Application Data

[62] Division of Ser. No. 545,809, Oct. 26, 1983, abandoned.

[51] Int. Cl.$^4$ .............................................. C07C 85/20
[52] U.S. Cl. ...................................... 564/386; 564/346
[58] Field of Search ................................. 564/386, 376

[56] References Cited

U.S. PATENT DOCUMENTS

| | | | |
|---|---|---|---|
| 2,167,351 | 7/1939 | Eisleb | 260/294 |
| 2,504,977 | 4/1950 | Gump et al. | 260/458 |
| 2,588,849 | 3/1950 | Kerwin et al. | 564/376 X |
| 2,601,275 | 6/1951 | Gamp et al. | 564/376 X |
| 2,653,156 | 9/1953 | Deutch et al. | 260/404 |
| 3,227,756 | 1/1966 | Richter et al. | 564/376 X |
| 3,271,435 | 9/1966 | Randall et al. | 564/386 X |
| 3,366,625 | 1/1968 | Hebky et al. | 564/386 X |
| 3,406,024 | 10/1968 | Richter et al. | 564/376 X |
| 4,011,344 | 3/1977 | Nadelson | 564/386 X |

OTHER PUBLICATIONS

E. Szarvasi et al., Eur. J. Med. Chem. Chim. Ther. 11(2), 115–24 (1976).
D. Thompson and P. C. Reeves, J. Heterocyclic Chem. 20, 771–2 (May–Jun. 1983).
Gutkowska, Acta Pol. Pharm. 30, 109–113 (1973) and English translation in part.
L. Rylski, F. Gajewski and Z. Kamonski, Acta Pol. Pharm. 31, 577–582 (1974) and English translation in part.

Primary Examiner—Robert V. Hines
Attorney, Agent, or Firm—Philip E. Hansen; Paul E. Dupont

[57] ABSTRACT

Improvements are shown in the successive preparations of N,N-bis(2-hydroxyethyl)benzylamine starting with benzyl chloride, its conversion to the corresponding N,N-bis(2-chloroethyl)benzylamine in substantially quantitative yield in toluene solution and using the latter by reaction with phenylacetonitrile in the presence of aqueous sodium hydroxide solution and a tetra-n-butylammonium salt, preferably the hydrogen sulfate, to produce improved over-all yields of up to over 75% (based on benzyl chloride) of 1-benzyl-4-cyano-4-phenylpiperidine hydrochloride, an intermediate for preparing meperidine.

6 Claims, No Drawings

PROCESS FOR PREPARING N,N-BIS(2-HYDROXYETHYL)BENZYLAMINE AND N,N-BIS(2-CHLOROETHYL)BENZYLAMINE

This application is a division of application Ser. No. 545,809; filed Oct. 26, 1983 and now abandoned.

BACKGROUND OF THE INVENTION (a) Field of the Invention

This invention relates to improvements in the process for preparing 1-benzyl-4-cyano-4-phenylpiperidine or hydrochloride acid-addition salt thereof, an intermediate for the preparation of meperidine, namely, ethyl 1-methyl-4-phenylpiperidine-4-carboxylate, commercially available in the form of its hydrochloride as an analgesic, spasmolytic and sedative (b) Information Disclosure Statement O. Eisleb in Example 2 of U.S. Patent 2,167,351, issued July 25, 1939, shows the preparation of 1-benzyl-4-phenylpiperidine-4-carbonitrile hydrochloride, m.p. 259°–260° C., as an intermediate for normeperidine, namely, ethyl 4-phenylpiperidine-4-carboxylate, by first reacting benzyl chloride with N,N-bis(2-hydroxyethyl)amine to produce N,N-bis(2-hydroxyethyl)benzylamine, next reacting the latter compound with thionyl chloride to produce N,N-bis(2-chloroethyl)benzylamine and isolating it in free base form as "an oil of feebly brownish color"; and then heating N,N-bis(2-chloroethyl)benzylamine with benzyl cyanide (same as phenylacetonitrile) in toluene in the presence of sodium amide (same as sodamide).

M. K. Deutch and H. W. Stobbe in Example 1 of U.S. Pat. No. 2,653,156, issued Sept. 22, 1953, show the preparation in 52% yield of N,N-bis(2-hydroxyethyl)benzylamine (as an intermediate for preparing its caprylate ester) by the action of one mole of benzyl chloride on one mole of N,N-bis(2-hydroxyethyl)amine "in the presence of potassium carbonate" and subsequent distillation under vacuum. The potassium carbonate is said to serve "as an acid acceptor and may be replaced by any suitable alkaline material capable of combining with the chlorine of the benzyl chloride, for example, alkali metal carbonates or bicarbonates such as sodium carbonate or bicarbonate, triethanolamine or pyridine".

E. Szarvasi et al., Eur. J. Med. Chem. Chim. Ther. 11(2), 115–24 (1976), in a paper pertaining to the preparation of spiro[piperidine-4,6-thiazolo[3,2-a]pyrimidines], dines], thymoanaleptics and blood platelet aggregation inhibitors, show inter alia at page 123, 2nd column: (a) the preparation of N,N-bis(2-hydroxyethyl)benzylamine (compound no. 1e, Table VIIIa, p. 121) in 89% yield, m.p. 168°–172° C., by rapidly adding 0.5 mole of benzyl chloride (or bromide) to a mixture of 0.5 mole of N,N-bis(2-hydroxyethyl)amine, 0.55 mole (or more than two molar equivalents) of potassium carbonate and 500 cc of toluene kept at about 60° to 70° C., heating the reaction mixture to reflux for four hours, filtering off the inorganic salts and washing them with a little toluene, and distilling the filtrate; and, (b) the preparation of N,N-bis(2-chloroethyl)benzylamine hydrochloride (compound no. 2e, Table VIIa, p. 121) in 98% yield, m.p. 148°–150° C., by the following procedure: To a solution of 0.295 mole of N,N-bis(2-hydroxyethyl)benzylamine in 225 cc of chloroform was added, so that the temperature was maintained between 30° and 40° C., a solution containing 0.710 mole of thionyl chloride in 50 cc of chloroform. The reaction mixture was refluxed for four hours; and, the precipitated hydrochloride of N,N-bis(2-chloroethyl)benzylamine was collected and recrystallized from ethanol.

W. S. Gump and E.J. Nikaivitz in Example 3 of U.S. Pat. No. 2,504,977 issued April 25, 1950, show the reaction of 190 g of benzyl chloride with 315 g of N,N-bis(2-hydroxyethyl)amine at 100–125° C. for nine hours followed by addition of sufficient saturated potassium carbonate to neutralize "the formed hydrochlorides" and continued stirring of the mixture for thirty minutes at 90° C. The separated oil in isopropyl ether and ethanol was dried and distilled twice to produce 162 g (54.3% yield) of pure N,N-bis(2-hydroxyethyl)benzylamine. A 97 g portion of N,N-bis(2-hydroxyethyl)benzylamine was converted into 115 g (85.7% yield) of N,N-bis(2-chloroethyl)benzylamine hydrochloride (46.5% yield based on benzyl chloride) by adding dropwise with stirring 120 g of thionyl chloride in chloroform to a cooled (ice bath) chloroform solution of N,N-bis(2-hydroxyethyl)benzylamine, and then isolating the product and converting it to its hydrochloride salt.

D. Thompson and P. C. Reeves, J. Heterocyclic Chem. 20, 771-2 (May-June 1983), show inter alia the reaction of phenylacetonitrile with N,N-bis(2-chloroethyl)benzylamine in 50% aqueous sodium hydroxide solution in the presence of a catalytic amount of various phase-transfer catalysts including benzyltriethylammonium chloride, tricaprylmethylammonium chloride, trialkyl $(C_8-C_{10})$methylammonium chloride, dicyclohexyl-18-crown-6, and hexadecyl tributylphosphonium bromide. These authors report:

"All of these catalysts are active, but the phosphonium catalyst is vastly superior to the others for this specific application. It produces high yields of the desired compounds in a short reaction time with only trace amounts of undesired by-products being formed."

These authors also state:

"The recent advent of phase-transfer catalysis has provided attractive alternatives to the use of hazardous bases such as sodium amide and anhydrous aprotic solvents. It has been demonstrated that phenylacetonitrile can be alkylated under phase-transfer conditions with 1,5-dibromopentane and bis(2-chloroethyl) ether to yield the corresponding six-membered rings [M. Makoska and B. Serafinowa, Rozc. Chem. 40, 1647 (1966)]. Attempts to extend this technique to the synthesis of nitrogen heterocycles have been plagued by very low yields [B. Gutowska, Acta Pol. Pharm. 30, 109 (1973) and L. Rylski, F. Gajewski and Z. Kamonski, ibid., 31, 577(1974)].

Gutkowska, Acta Pol. Pharm. 30, 109–113 (1973), shows the reaction of N,N-bis(2-chloroethyl)-n-butylamine with phenylacetonitrile in the presence of 50% aqueous sodium hydroxide solution and benzyltriethylammonium chloride as catalyst to produce 1-n-butyl-4-cyano-4-phenylpiperidine hydrochloride (30% yield).

L. Rylski, F. Gajewski and Z. Kamonski, Acta Pol. Pharm. 31, 577–582 (1974), show two methods for the conversion of N,N-bis(2-chloroethyl)benzylamine by reaction with phenylacetonitrile to produce 1-benzyl-4-cyano4-phenylpiperidine hydrochloride, the first method in a sodium hydroxide-toluene system resulting in a 63% yield of product melting at 253°–254° C. and the second method in a catalytic process using benzyltriethylammonium chloride in 50% aqueous sodium hydroxide resulting in a 61% yield of product melting at 254°-255° C. (Eisleb, supra, 259°-260° C.).

Heretofore, 1-benzyl-4-cyano-4-phenylpiperidine hydrochloride was produced commercially by first refluxing benzyl chloride in toluene with bis(2-hydroxyethyl)amine at about 105° C. to 115° C. for no less than 24 hour preferably 48 hours, and then in a second step adding thionyl chloride to the resulting N,N-bis(2-hydroxyethyl)benzylamine in toluene, quenching the reaction mixture with water followed by addition of aqueous sodium hydroxide solution, separating the toluene layer and azeotroping it to dryness to obtain a toluene solution containing about 70% yield (based on benzyl chloride) of N,N-bis(2-chloroethyl)benzylamine, and then in a third step treating portionwise a toluene solution of the latter and phenylacetonitrile with sodamide, quenching the reaction mixture with water, separating the toluene solution, distilling off in vacuo the toluene, dissolving the residual oil in methanol, acidifying the methanol solution with concentrated hydrochloric acid, collecting the precipitate, washing it with cold methanol and drying it to produce about a 57% yield [based on benzyl chloride] of 1-benzyl-4-cyano-4-phenylpiperidine hydrochloride. Analysis of the reaction mixture resulting from the first step of this preparation by gas chromatography/mass spectrography (GC/MS) revealed the presence of three major peaks in the ratio by weight of 53:13:16 (I:II:III) found to be respectively the desired intermediate, N,N-bis(2-hydroxyethyl)benzylamine (I) and two by-products, identified as N,N-dibenzyl-N-(2-hydroxyethyl)amine (II) and N-benzyl-N-(2-benzyloxyethyl)-N-(2-hydroxyethyl)amine (III). Comparable analysis of the second step of this preparation revealed the presence of another by-product, namely N-benzylmorpholine (about 5-10%). Virtual elimination of the formation of these three by-products is accomplished by the improved process of the invention.

SUMMARY OF THE INVENTION

In one of its aspects, the invention resides in an improved process for preparing N,N-bis(2-chloroethyl)benzylamine by first reacting benzyl chloride with bis(2-hydroxyethyl)amine to produce N,N-bis(2-hydroxyethyl)benzylamine and then reacting N,N-bis(2-hydroxyethyl)benzylamine with thionyl chloride to produce N,N-bis(2-chloroethyl)benzylamine, wherein the improvements comprise adding about one molar equivalent of benzyl chloride to a warmed mixture containing about one molar equivalent of N,N-bis(2-hydroxyethyl)amine and about one molar equivalent of sodium carbonate, the addition rate of benzyl chloride being so as to maintain the exothermic reaction temperature at about 70°-100° C.; maintaining the reaction temperature at about 70° to 100° C. for a short period; adding toluene to the reaction mixture; separating and drying the toluene solution containing N,N-bis(2-hydroxyethyl)benzylamine; adding said dry toluene solution to more than two molar equivalents of thionyl chloride heated to about 65° to 75° C., the rate of addition being so as to maintain the reaction temperature at about 65°-75° C.; treating the reaction mixture with aqueous alkali; and, separating the toluene solution containing a substantially quantitative yield of N,N-bis(2-chloroethyl)benzylamine, which can be used directly in the next step of the synthesis of 1-benzyl-4-cyano-4-phenylpiperidine hydrochloride.

In another aspect, the invention resides in an improved process for preparing N,N-bis(2-hydroxyethyl)benzylamine by reacting benzyl chloride with N,N-bis(2-hydroxyethyl)amine wherein the improvements comprise adding about one molar equivalent of benzyl chloride to a warmed mixture containing about one molar equivalent of N,N-bis(2-hydroxyethyl)amine and about one molar equivalent of sodium carbonate, the addition rate of benzyl chloride being so as to maintain the exothermic reaction temperature at about 70° to 100° C., maintaining the reaction temperature at about 70 to 100° C., preferably a 75° to 85° C., for a short period; adding toluene to the reaction mixture; cooling the mixture to about 50° to 65° C.; and, separating and drying the toluene solution containing a substantially quantitative yield of N,N-bis(2-hydroxyethyl)benzylamine.

Yet another aspect of the invention resides in an improved process for preparing N,N-bis(2-chloroethyl)benzylamine by reacting N,N-bis(2-hydroxyethyl)benzylamine with thionyl chloride to produce N,N-bis(2-chloroethyl)benzylamine, wherein the improvements comprise adding a dry toluene solution containing a molar equivalent of N,N-bis(2-hydroxyethyl)benzylamine to more than two molar equivalents of thionyl chloride heated to about 65°-75° C., the rate of addition being so as to maintain reaction temperature at about 65°-75° C.; treating the reaction mixture with aqueous alkali; and, separating the toluene solution containing a nearly quantitative yield of N,N-bis(2-chloroethyl)benzylamine.

In another aspect, the invention resides in an improved process for preparing 1-benzyl-4-cyano-4-phenylpiperidine hydrochloride by reacting N,N-bis(2-chloroethyl)benzylamine with phenylacetonitrile, wherein the improvement comprises reacting N,N-bis(2-chloroethyl)benzylamine in toluene with phenylacetonitrile in the presence of aqueous sodium hydroxide solution and a tetra-n-butylammonium salt.

DETAILED DESCRIPTION INCLUSIVE OF PREFERRED EMBODIMENTS

Aspects of this invention provide an improved procedure starting with benzyl chloride successively preparing substantially quantitative yields of first N,N-bis(2-hydroxyethyl)benzylamine and then N,N-bis(2chloroethyl)benzylamine, each in toluene solution and with no need to isolate either. Another aspect of the invention provides an improved process for converting N,N-bis(2-chloroethyl)benzylamine in toluene solution to 1-benzyl-4-cyano-4-phenylpiperidine hydrochloride in overall yields of up to over 75% based on benzyl chloride.

The improvements in the above process aspects of the invention which afford a substantially quantitative yield of N,N-bis(2-chloroethyl)benzylamine, are based in part on modifications which eliminate formation of by-products and in part on a reverse in the order of addition of reactants. One improvement is based on the use of a molar equivalent quantity of sodium carbonate in the reaction of bis(2-hydroxyethyl)amine with benzyl chloride to produce N,N-bis(2-hydroxyethyl)benzyl amine, thereby completely inhibiting formation of the by-products N,N-dibenzyl-N-(2-hydroxyethyl)amine and N-benzyl-N-(2-benzyloxyethyl)-N-(2-hydroxyethyl)amine, which are produced in relatively large quantities (about 16% and 20% respectively) in the absence of said sodium carbonate. Another improvement is based on the addition of N,N-bis(2-hydroxyethyl)benzylamine in toluene solution to slightly more than a two molar excess of thionyl chloride rather than the heretofore reverse addition of thionyl chloride to N,N-bis(2-hydroxyethyl)benzylamine, thereby completely eliminating the formation of N-benzylmorpholine. Another improvement is the azeotropic distillation of the toluene solution of N,N-bis(2-hydroxyethyl)benzylamine to remove the water formed by the reaction, thereby avoiding the use of excess thionyl chloride to ensure completion of reaction in the chlorination step.

In a preferred aspect of producing N,N-bis(2-chloroethyl)benzylamine, the improvements comprise adding one molar equivalent of benzyl chloride to a warmed mixture containing one molar equivalent of bis(2-hydroxyethyl)amine and one molar equivalent of sodium carbonate, the addition rate of benzyl chloride being so as to maintain the exothermic reaction temperature at about 70°–100° C.; maintaining the reaction temperature at about 70° to 100° C. for a short period (about one hour) after addition of the benzyl chloride to completion of the reaction (determined by gas chromatography); adding toluene to the reaction mixture; cooling the reaction mixture to about 50 to 65° C.; filtering the mixture to remove inorganics; washing the filter cake with toluene; dryinq the combined filtrate and washings by azeotropic distillation; adding the dry toluene solution to more than two molar equivalents (preferably about 2.2) of thionyl chloride heated to about 65° to 75° C., the rate of addition being so as to maintain the reaction temperature at about 65°–75° C.; adding successively to the reaction mixture water and concentrated alkali (preferably 35% aqueous sodium hydroxide solution); and, drawing off the heavier aqueous layer to produce a toluene solution containing a substantially quantitative yield of N,N-bis(2-chloroethyl)-benzylamine, which can be used directly in the next step of the synthesis of 1-benzyl-4-cyano-4-phenylpiperidine hydrochloride.

In a preferred aspect of the invention for preparing N,N-bis(2-hydroxyethyl)benzylamine, the improvements comprise adding about one molar equivalent of benzyl chloride to a warmed mixture containing one molar equivalent of N,N-bis(2-hydroxyethyl)amine and one molar equivalent of sodium carbonate, the addition rate of benzyl chloride being so as to maintain the exothermic reaction temperature at about 70° to 100° C., maintaining the reaction temperature at about 70° to 100° C., preferably a 75° to 85° C., for a short period until the reaction is complete; adding toluene to the reaction mixture; cooling the mixture to about 50° to 65° C.; filtering the mixture to remove inorganics; washing the filter-cake with toluene; drying the combined filtrate and washings by azeotropic distillation to produce a dry toluene solution containing a substantially quantitative yield of N,N-bis(2-hydroxyethyl)benzylamine.

In another preferred aspect of the invention for preparing N,N-bis(2-chloroethyl)benzylamine by reacting N,N-bis(2-hydroxyethyl)benzylamine with thionyl chloride to produce N,N-bis(2-chloroethyl)benzylamine, the improvements comprise adding a dry toluene solution containing a molar equivalent of N,N-bis(2-hydroxyethyl)benzylamine to more than two molar equivalents of thionyl chloride heated to about 65°–75° C., the rate of addition being so as to maintain the reaction temperature at about 65°–75° C., adding successively to the reaction mixture water and concentrated alkali; and, drawing off the heavier aqueous layer to produce a toluene solution containing a nearly quantitative yield of N,N-bis(2-chloroethyl)benzylamine.

The use of tetra-n-butylammonium salt, preferably the hydrogen sulfate or alternatively the bromide or chloride, in the reaction of bis(2-chloroethyl)benzylamine in toluene with phenylacetonitrile in the presence of aqueous sodium hydroxide results in yields of up to about 77% compared to much lower yields obtained using other quaternary ammonium salts. This aspect of the invention is preferably run by dissolving equimolecular amounts of N,N-bis(2-chloroethyl)benzylamine and phenylacetonitrile in toluene, adding 10 mole percent of tetran-butylammonium hydrogen sulfate, slowly adding with vigorous agitation four molar equivalents of 50% sodium hydroxide (over a short period, about 60 to 90 minutes), maintaining the agitated reaction mixture at about 65° to 85° C. until the reaction is completed (about three to four hours), quenching the reaction mixture with water, separating the toluene layer, washing it with water to neutral pH, distilling off the toluene in vacuo, dissolving the residue with a suitable solvent, e.g., methanol, acidifying the resulting solution with concentrated hydrochloric acid, collecting the precipitated product and drying it to obtain 1-benzyl-4-cyano-4-phenylpiperidine hydrochloride in yields up to about 77% based on benzyl chloride used in the preparation of N,N-bis(2-hydroxyethyl)benzylamine. In place of methanol other suitable solvents can be used, e.g., ethanol, acetone or isopropyl alcohol.

In contrast to the above results obtained using tetra-n-butylammonium hydrogen sulfate or bromide, poor results were obtained using the following quaternary ammonium salts: benzyltriethylammonium chloride (insoluble in the reaction mixture and resulting in only 12% of product after three hours at 75°–85° C); benzyl-tri-n-butylammonium chloride (only 6.5% of product formed after two hours at 75°–85° C.); and, benzyltrimethylammonium chloride (insoluble in the reaction mixture and only about 6% of product formed after two hours at 75°–85° C.):

In the aspect of the invention using a molar equivalent quantity of sodium carbonate in the reaction of bis(2-hydroxyethyl)amine with benzyl chloride to produce a substantially quantitive yield of N,N-bis(2-hydroxyethyl)benzylamine, when a molar equivalent quantity of either finely powdered potassium carbonate or sodium bicarbonate was substituted for the sodium carbonate, about 6% an O-benzyl impurity was formed in each instance with only 92% or 86% respectively of N,N-bis(2-hydroxyethyl)benzylamine being formed.

The following examples will further illustrate the invention without, however, limiting it thereto.

EXAMPLE 1

To 1500 g of N,N-bis(2-hydroxyethyl)amine was added 758 g of sodium carbonate and the mixture was heated with stirring to 50° C. To the stirred mixture was slowly added 1807 g of benzyl chloride, the addition rate of benzyl chloride being so as to maintain the reaction temperature at about 70° to 80° C. After addition had been completed, heating at 70° to 80° C. was continued with stirring for one hour. To the reaction mixture was added 1500 g of toluene; the resulting mixture was filtered; and, the filter cake was washed with three 500 g portions of toluene. A 55.3 g portion of the cloudy filtrate was stripped to dryness to produce 28.6 g N,N-bis(2-hydroxy)benzylamine (51.7%): The total yield of toluene solution was 5440 g, thus containing 2813 g or quantitative yield of N,N-bis(2-hydroxyethyl)benzylamine (gas chromatography of solution showed 98.44% of said compound). A 100 g portion of the toluene solution containing 51.7 g of N,N-bis(2-hydroxyethyl)benzylamine was dried by azeotropic distillation and then slowly added with stirring over a period of ninety minutes to 70 g of thionyl chloride, keeping the reaction mixture at about 65°–75° C. The reaction mixture was heated with stirring for another hour at about 65°–75° C. after addition of N,N-bis(2-hydroxyethyl)benzylamine had been completed. To the stirred reaction mixture were then added successively 100 ml of water and 70 ml of 35% aqueous sodium hydroxide solution. The layers were separated, the toluene layer was dried by azeotropic distillation and the resulting dry toluene solution was found by gas chromatography to contain a 94.0% yield of N,N-bis(2-chloroethyl)benzylamine, which solution is used directly in the next step in the synthesis of meperidine.

In another run following the above chlorination procedure using 1633 g of a dry toluene solution containing 990 g of N,N-bis(2-hydroxyethyl)benzylamine and 1390 g of thionyl chloride, there was obtained 2578.2 g of a toluene solution containing 45.25 g of N,N-bis(2-chloroethyl)benzylamine per 100 g of solution, thereby providing a total of 1166 g (99% yield based on benzyl chloride used) of N,N-bis(2-chloroethyl)benzylamine.

EXAMPLE 2

Into a jacketed, glass-lined kettle equipped with an agitator, condenser, recording thermometer, receiver, azeotrope leg and the usual services connected to a scrubber system was added 251 kg of molten N,N-bis(2-hydroxyethyl)amine followed by flushing of the line with 30 kg of toluene. To the agitated mixture was added 127.6 kg of sodium carbonate and the resulting mixture was warmed to about 50° C. To the agitated mixture was slowly added over a period of about 1 to 2 hours 302 kg of benzyl chloride, maintaining a reaction temperature of about 70° to 100° C. during the addition. After the addition had been completed, the reaction temperature was adjusted to about 80°–100° C. which was maintained for about one hour. To the reaction mixture was then added 220 kg (67 gal) of toluene; the resulting mixture was cooled to about 60°–65° C. and filtered. The filter cake was washed once with 220 kg (67 gal) of toluene and a second time with 165 kg (50 gal) of toluene. The combined filtrate and toluene washings were transferred back into the empty kettle that had contained the reaction mixture, the equipment was prepared for azeotropic distillation and the mixture was distilled until no water was observed in the leg. The mixture was then cooled to ambient temperature and filtered to produce a dry toluene solution of a nearly quantitive yield of N,N-bis(2-hydroxyethyl)benzylamine. The original reaction kettle was cleaned and was charged with 657 kg of thionyl chloride, which was heated to 65°–75° C. To the heated thionyl chloride was added with agitation over a three to four and one-half hour period the toluene filtrate containing N,N-bis(2-hydroxyethyl)benzylamine, while maintaining a reaction temperature of about 65°–75° C. After the addition had been completed, the temperature was maintained at about 65°–75° C. for about one hour with agitation. The reaction mixture was then cooled to about 55°–65° C. and to it was added, cautiously at first, 1500 kg (400 gal) of water and the temperature is adjusted to 30°–40° C. After addition had been completed, the mixture was agitated at 30°–40° C. for a minimum of thirty minutes. A jacketed, iron kettle equipped with agitator, recording thermometer, condenser and the usual services connected to a scrubber system was charged with 466 kg (90 gal) of 35% aqueous sodium hydroxide solution and 100 gal. (378 kg) of water. The reaction mixture was transferred to the kettle containing the aqueous sodium hydroxide solution and the resulting mixture was agitated without cooling for a minimum of forty-five minutes. The mixture was then transferred to an iron separator and allowed to stand for a minimum of one hour without agitation. The toluene layer was separated by drawing of the heavier aqueous layer and was found to contain a nearly quantitative yield of N,N-bis(2-chloroethyl)benzylamine. This solution was used directly in the next step in the synthesis of meperidine.

EXAMPLE 3

To a well stirred solution containing 145 g of a dry toluene solution of 78.5 g of N,N-bis(2-chloroethyl)benzylamine, 39.8 g of phenylacetonitrile and 11.55 g of tetra-n-butylammonium hydrogen sulfate was slowly added over a thirty minute period 109 g of 50% (w/w) aqueous sodium hydroxide solution whereupon the temperature of the exothermic reaction rose to about 65° to 70° C. The reaction mixture was heated at about 65° to 70° C. for five hours. Samples were removed at one hour intervals and analyzed gas chromatographically with the following results:

| Time After Addition | Sample No. | Percent $C_6H_5CH_2CN$ | Percent amine[a] | Percent piperidine[b] |
|---|---|---|---|---|
| 0 hr. | 1 | 27.6 | 27.1 | 42.2 |
| 1 hr. | 2 | 12.8 | 12.7 | 70.1 |
| 2 hrs. | 3 | 7.8 | 7.0 | 80.8 |
| 3 hrs. | 4 | 6.0 | 5.0 | 84.0 |
| 4 hrs. | 5 | 4.1 | 2.8 | 87.0 |
| 5 hrs. | 6 | 3.0 | 2.3 | 85.5 |

[a] N,N—bis(2-chloroethyl)benzylamine.
[b] 1-Benzyl-4-cyano-4-phenylpiperidine.

To the reaction mixture was added 100 ml of water; the layers were separated; the toluene layer was washed three times with water (to neutral pH) and distilled in vacuo to remove the toluene; the residue was dissolved in 100 g of methanol; and, the methanol solution was acidified with concentrated hydrochloric acid and cooled in an ice-methanol bath. The crystalline product was collected, washed with cold methanol and dried to yield 72.6 g (68.3% based on N,N-bis(2-chloroethyl)benzylamine) of 1-benzyl 4-cyano-4-phenylpiperidine hydrochloride, m.p. 261°–264° C.

In another run following the procedure described in Example 3 using 151.2 g of toluene solution containing 78.5 g of N,N-bis(2-chloroethyl)benzylamine, 39.8 g of phenylacetonitrile, 109 g of 50% aqueous sodium hydroxide solution, 11.6 g of tetra-n-butylammonium hydrogen sulfate, adding the sodium hydroxide solution over a period of twenty minutes and heating the reaction mixture at 85° C. for four hours, there was obtained 74.1 g (70% yield based on N,N-bis(2-chloroethyl)benzylamine) of 1-benzyl-4-cyano-4-phenylpiperidine hydrochloride, m.p. 261°–263° C.

Following the procedure described above in Example 3 using in place of tetra-n-butylammonium hydrogen sulfate a molar equivalent quantity of tetra-n-butylammonium bromide, there was produced three hours after addition of the sodium hydroxide solution 83.4% of 1-benzyl-4-cyano-4-phenylpiperidine as determined by gas chromatographic analysis. Using a molar equivalent quantity of tetra-n-butylammonium chloride in place of the hydrogen sulfate or bromide in said procedure, it is contemplated that corresponding results would be obtained. Using a molar equivalent quantity of the corresponding iodide salt in said procedure produced lower yields of product, that is, 48.2%, 58% and 77% respectively three, four and five hours after addition of the sodium hydroxide solution.

EXAMPLE 4

Into a jacketed, iron kettle equipped with an agitator, recording thermometer, condenser and the usual services connected to a scrubber system was added a dry toluene solution containing 250 kg of toluene and 558 kg of N,N-bis(2-chloroethyl)benzylamine. Another 330 kg (100 gal) of toluene was added, followed by 279 kg of phenylacetonitrile and 81 kg of tetra-n-butylammonium hydrogen sulfate. To the agitated reaction mixture warmed to about 50° C. was slowly added over a period of about 60 to 90 minutes 766 kg of 50% (w/w) aqueous sodium hydroxide solution. Then the reaction mixture was agitated while maintaining the reaction temperature at about 75° to 85° C. for about four hours. To the reaction mixture was next added 450 gallons of water and the resulting mixture agitated for about fifteen minutes. The mixture was transferred to an iron separator and allowed to stand for a minimum of one hour. The heavier water layer was drawn off and discarded. To the toluene solution was added 450 gallons of water and the mixture agitated well. The heavier water layer was drawn off and discarded. This water washing treatment was repeated two more times. The washed toluene layer was filtered through diatomaceous earth and the filtrate was distilled at about 67° C. under about 22 inches of vacuum to remove the toluene. The residue was dissolved by agitating it with 400 kg (504 liters) of methanol and the solution cooled to about 40° C. To the methanol solution maintained at a temperature below 35° C. was added about 244–300 kg; 55–68 gal) of concentrated hydrochloric acid until the solution was acid to Congo Red Test Paper (pH of 3 or less). The solution was agitated for a minimum of thirty minutes and cooled to below 0° C. for a minimum of three hours The precipitated product was collected by centrifuging and was washed with 300 kg (378 1) of methanol cooled to about 0° C. There was thus obtained 1-benzyl-4-cyano-4-phenylpiperidine hydrochloride.

Representative runs following the above procedures presented in Examples 2 and 4 gave the following overall yields of product based on the benzyl chloride used:

| Yield[a], kg | Percent Yield[b] | M.pt., °C. | Product Assay, % |
|---|---|---|---|
| 497 | 66.5 | 261–262.5 | 98.2 |
| 495.4 | 66.3 | 261–263 | 98.1 |
| 501.8 | 67.2 | 260–263.5 | 98.1 |
| 518.4 | 69.4 | 261.5–265 | 97.2 |
| 507.8 | 68.0 | 262.5–264.5 | 99.5 |
| 514.4 | 68.9 | 263–265 | 99.0 |
| 514.2 | 68.8 | 262–264 | 97.7 |
| 523.4 | 70.1 | 261.5–263 | 99.7 |
| 529.4 | 70.9 | 261–264 | 98.8 |
| 510.4 | 68.3 | 263–264 | 98.8 |
| 513 | 68.7 | 262–264 | 98.9 |
| 531.4 | 71.3 | 261–263.5 | 97.7 |
| 506.4 | 69.8 | 262.5–265 | 98.5 |
| 574.2 | 76.9 | 262–264.5 | 98.9 |

[a]Yield of 1-benzyl-4-cyano-4-phenylpiperidine hydrochoride.
[b]Yield based on benzyl chloride.

We claim:

1. In the process for preparing N,N-bis(2-chloroethyl)benzylamine by first reacting benzyl chloride with N,N-bis(2-hydroxyethyl)amine to produce N,N-bis(2-hydroxyethyl)benzylamine and then reacting N,N-bis(2-hydroxyethyl)benzylamine with thionvl chloride to produce N,N-bis(2-chloroethyl)benzylamine, the improvements which comprise adding about one molar equivalent of benzyl chloride to a warmed mixture containing about one molar equivalent of N,N-bis(2-hydroxyethyl)amine and about one molar equivalent of sodium carbonate, the addition rate of benzyl chloride being so as to maintain the exothermic reaction temperature at about 70° to 100° C.; maintaining the reaction temperature at about 70° to 100° C. for a short period; adding toluene to the reaction mixture; separating and drying the toluene solution containing N,N-bis(2-hydroxyethyl)benzylamine; adding said dry toluene solution to more than two molar equivalents of thionyl chloride heated to about 65°–75° C., the rate of addition being so as to maintain the reaction temperature at about 65°–75° C.; treating the reaction mixture with aqueous alkali; and, separating the toluene solution containing a substantially quantitative yield of the N,N-bis(2-chloroethyl)benzylamine.

2. The process according to claim 1 which comprises adding one molar equivalent of benzyl chloride to a warmed mixture containing one molar equivalent of N,N-bis(2-hydroxyethyl)amine and one molar equivalent of sodium carbonate, the addition rate of benzyl chloride being so as to maintain the exothermic reaction temperature at about 70° to 100° C.; maintaining the reaction temperature at about 70° to 100° C. for a short period; adding toluene to the reaction mixture; cooling the mixture to about 50° to 65° C., filtering the mixture to remove inorganics; washing the filtercake with toluene; drying the combined filtrate and washings by azeotropic distillation; adding the dry toluene solution to more than two molar equivalents of thionyl chloride heated to about 65°–75° C., the rate of addition being so as to maintain the reaction temperature at about 65°–75° C.; adding successively to the reaction mixture water and concentrated alkali; and, drawing off the heavier aqueous layer to produce a toluene solution containing a substantially quantitative yield of N,N-bis(2-chloroethyl)benzylamine.

3. In the process for preparing N,N-bis(2-hydroxyethyl)benzylamine by reacting benzyl chloride with N,N-bis(2-hydroxyethyl)amine the improvements which comprise adding about one molar equivalent of benzyl chloride to a warmed mixture containing about one molar equivalent of N,N-bis(2-hydroxyethyl)amine and about one molar equivalent of sodium carbonate, the addition rate of benzyl chloride being so as to maintain the exothermic reaction temperature at about 70° to 100° C.; maintaining the reaction temperature at about 70° to 100° C. for a short period; adding toluene to the reaction mixture; and, separating and drying the toluene solution containing a substantially quantitative yield of N,N-bis(2-hydroxyethyl)benzylamine.

4. The process according to claim 2 which comprises adding one molar equivalent of benzyl chloride to a warmed mixture containing one molar equivalent of N,N-bis(2-hydroxyethyl)amine and one molar equivalent of sodium carbonate, the addition rate of benzyl chloride being so as to maintain the exothermic reaction temperature at about 70° to 100° C.; maintaining the reaction temperature at about 70° to 100° C. for a short period; adding toluene to the reaction mixture; cooling the mixture to about 50° to 65° C.; filtering the mixture to remove inorganics; washing the filter-cake with toluene; drying the combined filtrate and washings by azeotropic distillation to produce a dry toluene solution containing a substantially quantitative yield of N,N-bis(2-hydroxyethyl)benzylamine.

5. In the process for preparing N,N-bis(2-choroethyl)benzylamine by reacting N,N-bis(2-hydroxyethyl)benzylamine with thionyl chloride to produce N,N-bis(2-chloroethyl)benzylamine, the improvements which comprise adding a dry toluene solution containing a molar equivalent of N,N-bis(2-hydroxyethyl)benzylamine to more than two molar equivalents of thionyl chloride heated to about 65°–75° C., the rate of addition being so as to maintain the reaction temperature at about 65°–75° C.; treating the reaction mixture with aqueous alkali; and, separating the toluene solution containing a nearly quantitative yield of N,N-bis(2-chloroethyl)benzylamine.

6. The process according to claim 5 which comprises adding a dry toluene solution containing a molar equivalent of N,N-bis(2-hydroxyethyl)benzylamine to more than two molar equivalents of thionyl chloride heated to about 65°–75° C., the rate of addition being so as to maintain the reaction temperature at about 65°–75° C.; adding successively to the reaction mixture water and concentrated alkali; and, drawing off the heavier aqueous layer to produce a toluene solution containing a nearly quantitative yield of N,N-bis(2-chloroethyl)benzylamine.

* * * * *

UNITED STATES PATENT AND TRADEMARK OFFICE
CERTIFICATE OF CORRECTION

PATENT NO. : 4,748,276

DATED : March 6, 1985

INVENTOR(S) : John R. Handley and Allen F. Dow

It is certified that error appears in the above-identified patent and that said Letters Patent is hereby corrected as shown below:

Column 5, line 49, "a" should read --about--.

Column 5, line 56, "vield" should read --yield--.

Column 6, line 13, "tetran-butylammonium" should read --tetra-n-butylammonium--.

Column 10, line 14, "thionvl" should read --thionyl--.

Column 10, line 45, "drving" should read --drying--.

Column 11, line 12, "drving" should read --drying--.

Signed and Sealed this

Thirteenth Day of December, 1988

Attest:

DONALD J. QUIGG

*Attesting Officer*     *Commissioner of Patents and Trademarks*